(12) United States Patent
Allen et al.

(10) Patent No.: US 8,288,154 B2
(45) Date of Patent: Oct. 16, 2012

(54) NANOMOTION SENSING SYSTEM AND METHOD

(75) Inventors: Michael John Allen, Alameda, CA (US); Lucien Ghislain, Daly City, CA (US)

(73) Assignee: Alegis Microsystems, Alameda, CA (US)

( * ) Notice: Subject to any disclaimer, the term of this patent is extended or adjusted under 35 U.S.C. 154(b) by 0 days.

(21) Appl. No.: 10/690,809

(22) Filed: Oct. 21, 2003

(65) Prior Publication Data

US 2004/0142409 A1   Jul. 22, 2004

Related U.S. Application Data

(60) Provisional application No. 60/420,078, filed on Oct. 21, 2002.

(51) Int. Cl.
*C12M 1/34* (2006.01)
*C12M 3/00* (2006.01)
*G01N 33/53* (2006.01)

(52) U.S. Cl. .................. 435/287.1; 435/288.7; 435/7.1; 435/7.2; 435/29; 435/34; 435/287.9; 73/61.41; 73/61.71; 73/61.75; 422/68.1; 250/573; 250/574

(58) Field of Classification Search ............... 435/287.1, 435/288.7, 7.1, 7.2, 29, 287.9, 34; 73/61.41, 73/61.71, 61.75; 422/68.1; 250/573, 574
See application file for complete search history.

(56) References Cited

U.S. PATENT DOCUMENTS

| | | | |
|---|---|---|---|
| 4,202,747 A | 5/1980 | Buzza et al. | |
| 4,300,906 A | 11/1981 | Negersmith | |
| 5,536,963 A * | 7/1996 | Polla | 257/417 |
| 5,620,854 A | 4/1997 | Holzrichter et al. | |
| 5,952,657 A | 9/1999 | Alexander et al. | |
| 6,016,686 A | 1/2000 | Thundat | |
| 6,054,277 A | 4/2000 | Furcht et al. | |
| 6,280,939 B1 | 8/2001 | Allen | |
| 6,289,717 B1 * | 9/2001 | Thundat et al. | 73/23.2 |
| 6,631,648 B2 | 10/2003 | Lal et al. | |
| 6,642,517 B1 * | 11/2003 | Ghislain et al. | 250/306 |
| 6,935,165 B2 * | 8/2005 | Bashir et al. | 73/64.53 |
| 2001/0011704 A1 | 8/2001 | Niwa et al. | |

(Continued)

FOREIGN PATENT DOCUMENTS

WO    WO-01/01121 A1 *   1/2001

OTHER PUBLICATIONS

Lang, H.P., "An Artificial Nose Based on a Micromechanical Cantilever Array", *Physical Sciences*, pp. 1-7 (Oct. 19, 1998).
C. Hagleitner, A. Hierlemann, D. Lange, A Kummer, N. Kerness, O. Brand & H. Baltes; Smart single-chip gas sensor microsystem; Physical Electronics Laboratory, ETH Zurich, Honggerberg, HPT H 6, CH-8093 Zurich, Switzerland (Nature 414, Nov. 15, 2001, 293-296.

*Primary Examiner* — Nathan Bowers (57) ABSTRACT

A Nanomotion Sensor comprises a micromechanical device for the detection and characterization of specimen motions when they interact with one or an array of cantilevered sensors set in the path of the moving specimen. In particular, the present invention provides a method for direct sensing and characterization of motion, including position, torsion, magnitude and direction of velocity, acceleration, force, torque, as well as binding, which may include hydrogen bonding, electrostatic attractions, hydrophobic effects, dipole interactions, or through other forces through the deflection of a micromechanical cantilever sensor. The present invention is particularly useful for the detection and characterization of the motion of biological cells such as bacteria and sperm, biological systems including motor proteins, cilia of the hearing organ and the lining of the airways in asthmatics, and microfabricated systems.

13 Claims, 8 Drawing Sheets

U.S. PATENT DOCUMENTS

| | | |
|---|---|---|
| 2002/0092340 A1* | 7/2002 | Prater et al. ............... 73/24.02 |
| 2002/0118005 A1 | 8/2002 | Reich et al. |
| 2003/0045019 A1 | 3/2003 | Kubena |
| 2003/0209656 A1* | 11/2003 | Paritsky et al. ............ 250/231.1 |
| 2003/0222232 A1* | 12/2003 | Welland et al. ............... 250/573 |
| 2005/0121615 A1* | 6/2005 | Prater et al. .................. 250/343 |
| 2005/0239047 A1* | 10/2005 | Gimzewski et al. ............... 435/4 |
| 2011/0020834 A1* | 1/2011 | Craighead et al. ............. 435/7.1 |

* cited by examiner

NANOMOTION SENSING SYSTEM AND METHOD

The present application claims the benefit of priority under 35 U.S.C. §119(e) from U.S. Provisional Patent Application No. 60/420,078 filed on Oct. 21, 2002 to the present inventors air, and entitled "Integrated Nanosensor", which application is incorporated herein by reference.

I FIELD OF THE INVENTION

The present invention relates to the field of force-transducing sensors for determining the properties of samples containing many specimens such as biological cells immersed in a fluid, which include but are not limited to motion, position, frequency, phase, retention time, flow rate, viscosity, hydrodynamic drag, temperature, binding, momentum, magnitude and direction of velocity, migration time, chemotaxis, acceleration, force, energy, torsion, torque as well as the modifying effects caused by chemisorption, physisorption, hydrogen bonding, electrostatic attractions, hydrophobic effects, dipole interactions, magnetic, and other biological forces.

II BACKGROUND OF THE INVENTION

Berger et al ["Nanometers, Picowatts, Femtojoules: Thermal Analysis and Optical Spectroscopy Using Micromechanics," Analytical Methods & Instrumentation, Special Issue, uTAS '96] disclose examples of low-cost, disposable MEMS devices which perform optical absorption spectra, calorimetric and thermal analysis, electrochemical stressograms, gas phase adsorption and surface reaction monitors.

Cantilevers are used in atomic force microprobes which are able to move at high speed Minne et al ["Automated parallel high-speed atomic force microscopy," Applied Physics Letters, Volume 78, No. 18, May 4, 1998] also describe multiple atomic force microprobes operating in parallel for use in an atomic force microscope.

Manalis et al ["Interdigital cantilevers for atomic force microscopy," Applied Physics Letters, Vol. 69, No. 25, Dec. 16, 1996], disclose an atomic force microscopy (AFM) sensor in which a silicon cantilever is micromachined into the shape of interdigitated fingers that form a diffraction grating which allows the cantilever displacement to be determined by measuring the intensity of diffracted modes.

Lang et al ["Sequential position readout from arrays of micromechanical cantilever sensors," Applied Physics Letters, Vol. 73, p. 383, 1998] describe a reference cantilever for canceling environmental noise, where chemically specific responses are extracted statically in a noisy environment using a sensor cantilever to detect specific chemical interactions and an uncoated cantilever as a reference.

A conventional method for determining cell motility is also known in the art. In U.S. Pat. No. 6,238,874 entitled "Cell Motility Assay" a detection scheme is described which involves positioning a labeled fluorescence marker on a specimen and measuring its motion through the use of an excitation radiation source and radiation optics.

Prior art cantilever deflection sensors require cumbersome manipulation, for example, by use of mechanical stages, and use of optical alignment of a laser beam and a position-sensitive detector relative to the cantilever. Such manipulation and alignment is time consuming and increases the complexity of the system operation, which increases costs by requiring trained technicians to operate the system.

Although cantilevers have been known for many years, they have never before been applied to determining the miniscule motion of specimens in fluids, of great interest to biology and other technologies.

III SUMMARY OF THE INVENTION

The present invention includes two general types of nanomotion sensing systems. The nanomotion sensor (NMS) is composed of various components which are not affixed to each other, while an Integrated NMS is composed of various components which are affixed to each other in order to form a compact, robust and low cost system.

Both the (NMS) and the Integrated NMS as described herein has many advantages for detecting microscopic motion of a specimen in a medium. Various aspects related to motion can be detected such as position, frequency, phase, retention time, flow rate, viscosity, hydrodynamic drag, temperature, binding affinity, momentum, magnitude and direction of velocity, migration time, chemotaxis, acceleration, force, energy, torsion, torque as well as the modifying effects caused by chemisorption, physisorption, hydrogen bonding, electrostatic attractions, hydrophobic effects, dipole interactions, magnetic, and other forces. Various mediums can be used to enclose the sample, such as air, gas, vacuum, liquid, gel or any combination thereof. This is particularly important for specimens such as biological materials suspended in fluids and adsorbed on coatings, where the NMS is uniquely qualified to determine the dynamic properties of the biological materials.

The use of MEMS or related technology to create the NMS is advantageous since various signals such as force, heat, stress, magnetism, charge, radiation and chemical reactions can be readily transduced into a micromechanical deflection of a cantilever or other mechanical sensor and thereby measured accurately by the NMS.

As a result, it is possible with the present invention to produce an NMS at low cost and to connect the NMS output to a computer system for purposes of complete analysis.

A cantilever that might be used in the NMS is very small, and typically has a length in the range between 10 um and 1000 um, with an exemplary length being 200 um, a width in the range of 1 um to 100 um, which in one example is of the order of 50 um, and a thickness which may range from 0.1 to 10 um, and which in an exemplary arrangement may be of the order of 1 um. As a result of the small dimensions, it is possible to obtain a short response time, generally measured in range from milliseconds to microseconds, as well as sensitivities far superior to standard techniques. The small size of the NMS cantilever of the present invention provides an ability to directly measure small forces as applied, for example, by biological cells contacting a surface. Finally, it is possible to construct arrays of NMS force-sensing devices in accordance with the present invention that can be supported by micro-fluidic or milli-fluidic devices integrated with the NMS, thereby permitting complex analysis of a variety of signals as well as the use of a variety of sensing materials.

An Integrated NMS in accordance with the present invention has a promising future in research and development and in manufacturing, medical diagnostics, bio-analytical, quality control, and high-sensitivity testing environments because of its unique capabilities for detection and characterization of specimen motion and binding by measurement of small forces. The Integrated NMS of the present invention also offers the advantages of operating automatically with a minimum of user intervention, is versatile, i.e., being able to operate in air, aqueous environments or vacuum and is reliable, simple, compact and low cost.

There are two modes of operating the NMS or Integrated NMS, either in a Scanning Mode (SaM), which measures and analyzes the surface of a specimen as in an atomic force microscope (AFM) or a NMS Mode which senses specimen motion and binding via a change in cantilever position.

The SaM mode allows analysis of specimen properties including, but not limited to, topography, friction, electrostatics, magnetism, materials properties, force spectroscopy and ligand/receptor binding as the sample and/or the proximal cantilever/tip are scanned with respect to one another.

The NMS mode allows analysis of specimens in motion including, but not limited to position, frequency, phase, retention time, binding, flow rate, viscosity, temperature, magnitude and direction of velocity, acceleration, force, energy, torsion and torque. Binding includes chemisorption or physisorption to the cantilever by hydrogen bonding, electrostatic attractions, hydrophobic effects, dipole interactions, or through other forces.

The present invention provides an instrument and method for sensing and characterizing a specimen in motion such as a biological cell in a fluid, viruses, molecular and macromolecular assemblies, and other biomaterials. Once inside the nanomotion sensing chamber, the moving specimen is given an opportunity to interact with one or more force transducing sensors positioned in the path of the specimen. Surface interactions capable of generating a detectable change in the position or motion of the sensors are recorded by monitoring the sensor, for example, with a laser beam which is reflected to a position-sensitive photodiode. The cantilever is made of any material or coating and of any physical geometry and dimensions that results in a NMS capable of detecting motion of a specimen and/or binding of a specimen in motion.

In addition, other motion-related aspects are detectable such as frequency, phase, retention time, flow rate, viscosity, temperature, magnitude and direction of velocity, acceleration, force, energy, torsion and torque. In particular, the retention time of a specimen such as a biological cell on a cantilever can be altered by coating all or part of its surface thereby changing its ability to bind the specimen. Various bonding forces that may be involved include chemisorption, physisorption, by hydrogen bonding, electrostatic attractions, hydrophobic effects, dipole interactions, etc.

The present invention is particularly useful for the detection and characterization of the motion of fluids, gases, and microfabricated systems as they move through the sensing chamber and interact with a particular surface of a sensor or array of sensors. The invention is designed for specimens moving under their own power (i.e., self propelled) or carried along by a moving medium, including, but not limited to, a uniform flow of medium or a discontinuous flow of medium.

Various objects of the invention relate to the design and method of manufacture of an Integrated NMS. These include the following: (a) a method for sensing the orientation of a micromachined cantilever beam with an optical-beam-deflection sensor that includes a means for passive alignment of the cantilever beam to the optical-beam-deflection sensor, (b) a system for sensing the orientation of a micromachined cantilever beam with an optical-beam-deflection sensor where the micromachined cantilever beam and optical-beam-deflection sensor are actively aligned and then permanently bonded together to form an Integrated NMS, (c) a system for sensing the orientation of a micromachined cantilever beam with an optical-beam-deflection sensor that includes a means for automated active alignment of the cantilever beam relative to the optical-beam-deflection sensor, (d) a cantilever deflection sensor system which is more compact and less expensive to manufacture, (e) an atomic force microscope sensor system which is more compact and less expensive to manufacture, (f) a physical motion sensor system which is more compact and less expensive to manufacture, and (g) a chemical change sensor system which is more compact and less expensive to manufacture.

These and other objects, advantages, and features of the present invention are provided by an Integrated NMS that relies on passive alignment of the various components. The Integrated NMS preferably includes an optically transparent, substrate having first and second faces. The transparent substrate may include diffractive, refractive or reflective optical elements formed a surface of the transparent substrate. An optical light source, such as a laser and an position-sensing detector can be provided on a second substrate, the support substrate, and passive alignment means can be positioned between a surface of the transparent substrate and the support substrate for passively aligning the two substrates. The light source and the position-sensing detector can thus be aligned with respect to a transparent substrate. More particularly, the light source transmits light through the transparent substrate, through the diffractive or refractive optical element, and toward the cantilever. The cantilever substrate can be aligned relative to the transparent substrate and support substrate. The position-sensing detector detects light reflected from the cantilever through a second diffractive or refractive optical element, and through the transparent substrate. Accordingly, the laser and position-sensitive detector on the support substrate may be aligned with the optical elements on the second surface of the transparent substrate and, in turn, the cantilever on the cantilever substrate may be aligned with the optical elements on the transparent substrate, and the laser and position-sensitive detector on the support substrate.

The Integrated NMS and the related methods according to the present invention overcomes the disadvantages of the prior art and advantageously provides a significantly smaller system size for fabrication without the need for exciting or turning on the laser light source to actively align the components. Such a device would require very little training and minimal maintenance of parts.

V. DETAILED DESCRIPTION OF THE INVENTION

According to the present invention, a change in cantilever position or vibration is measured in order to detect and characterize the motion of biological cells (bacteria, sperm), biological systems including motor proteins, or cilia (of the hearing organ, of the lining of the airways in asthmatics).

Typically, a cantilever, which is but one form of a NMS sensor, as used with the method of the present invention When a specimen interaction occurs with the cantilever, a change occurs causing the cantilever to be deflected, e.g., moved up or down at its free end. Such deflection motion can be detected to a very fine degree, for example, down to a fraction of a diameter of an atom. A specimen interaction with the cantilever can also be detected by monitoring any change in the vibrational characteristics of a cantilever that is being excited in any manner that makes it oscillate.

Figure 1:
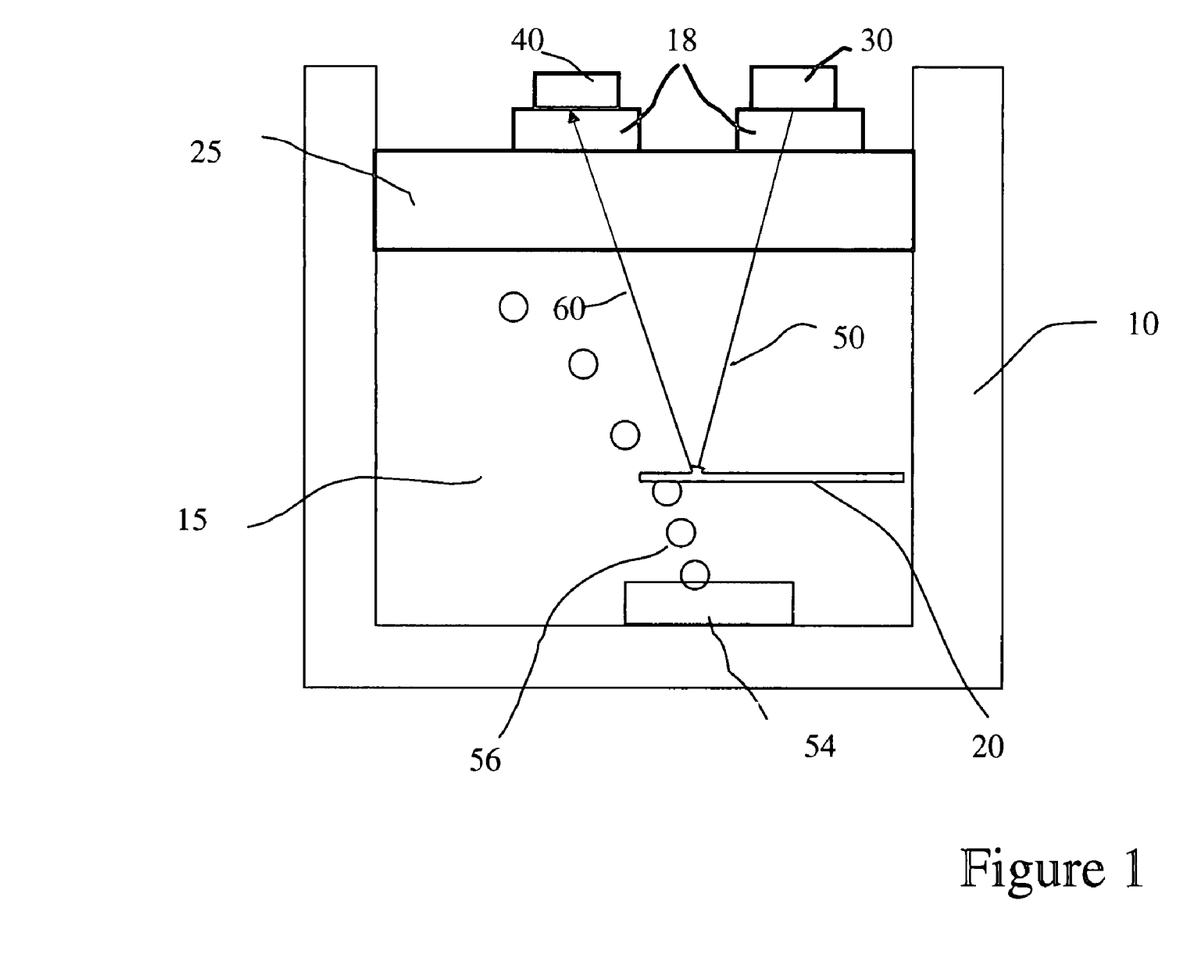
FIG. 1 is a schematic view of a nanomotion sensor.

As shown in FIG. 1, a cantilever 20 is provided which is on the order of a length in the range between 10 um and 1000 um and preferably 400 um long, has a width in the range between 5 um and 100 nm and preferably 75 um wide and has a thickness which is in the range of 0.5 um to 10 um and preferably 1 um thick Cantilever 20 is mounted into an enclosure 10, containing a fluid 15. A laser 30 is mounted on a Mechanical XY and Tilt Stage 18 and is located such that it has an incident beam 50 that is directed towards cantilever 20 and reflects off it. A reflected beam 60 thereby produced is incident on a photodetector 40 that is mounted on a similar Mechanical XY and Tilt Stage 18.

In the preferred embodiment, photodetector 40 can be generalized to any type of optical detector capable of tracking reflected laser light as known to one of ordinary skill in the art; for example, it can be a split photodiode, an array of photodetectors, thermal detectors, piezo resistive detectors, or the like.

A sample containing specimens such as cells 54, which can be biological cells suspended in fluid 15, is introduced 56 to the NMS sensing point, by either of three main ways—(a) immotile cells immersed in continuously flowing fluid, or (c) immotile cells immersed in a pulsed fluid like a P-shooter or (b) motile cells released in static, continuously flowing, or pulsed fluid, or any combination thereof. By monitoring the dynamic signal of the photodetector 40 it is possible to infer the movements of cantilever 20, which can be related to the individual properties of cells 56 that impinge on it.

This demonstrates a unique feature of the NMS, where cantilever 20 is immersed in a fluid 15 containing cells 56 to produce an output of photodetector 40 which can be used to detect the motion of cells 56 and the surface interaction between cells 56 and cantilever 20.

Figure 2:
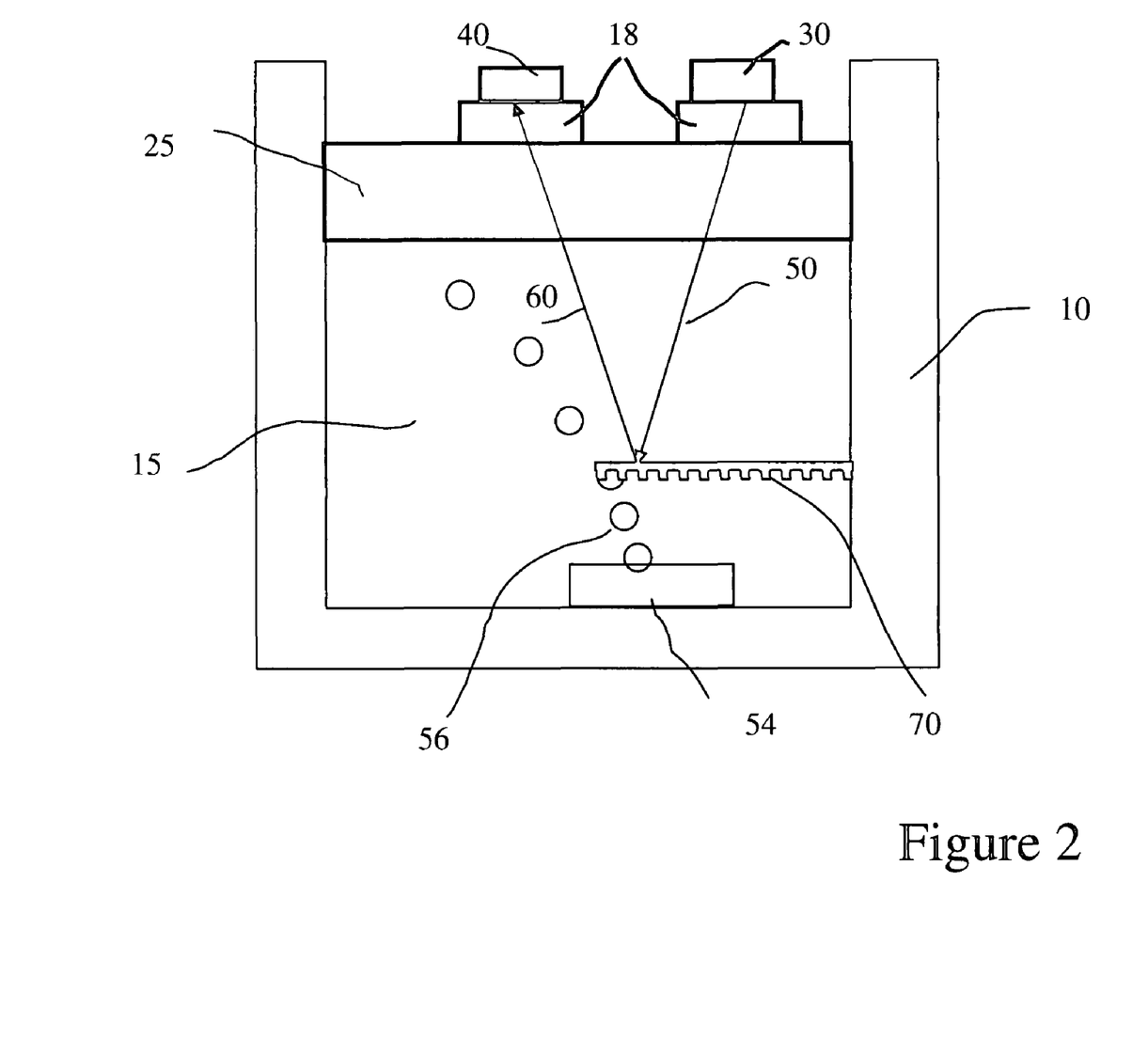
FIG. 2 is a schematic view of a nanomotion sensor with a cantilever having a surface treatment layer.

In another embodiment of the invention, as shown in FIG. 2, a treated cantilever 70 has its surface treated by a surface preparation allowing the adsorption or binding of biological cells and large molecules, for example. Such surface preparations are known to those of skill in the art of biological assays. More specifically, treated cantilever 70 is composed of a solid substrate, for example silicon, silicon nitride or similar materials which is coated with special surfaces (e.g. gold, carbon linkers) and which allow attachment of probe molecules and materials. Next, putative binding partners, such as those on the surface of biological cells, are introduced for binding with the surface of cantilever 70. Following detection of binding of a particular retention time of the moving cells 56 (i.e., the specimen moves due to a carrier fluid which is induced to flow into and through the NMS chamber), the adsorbed cells 56 can then be collected from cantilever 70 either by breaking cantilever 70 from the NMS and retrieving the adsorbed cells 56, or by aspiration of the adsorbed cells 56 into a side port of the sensing chamber (not shown). This embodiment of retrieving a sample of interest from the NMS sensing point is a very important and significant aspect of the invention.

Figure 3:
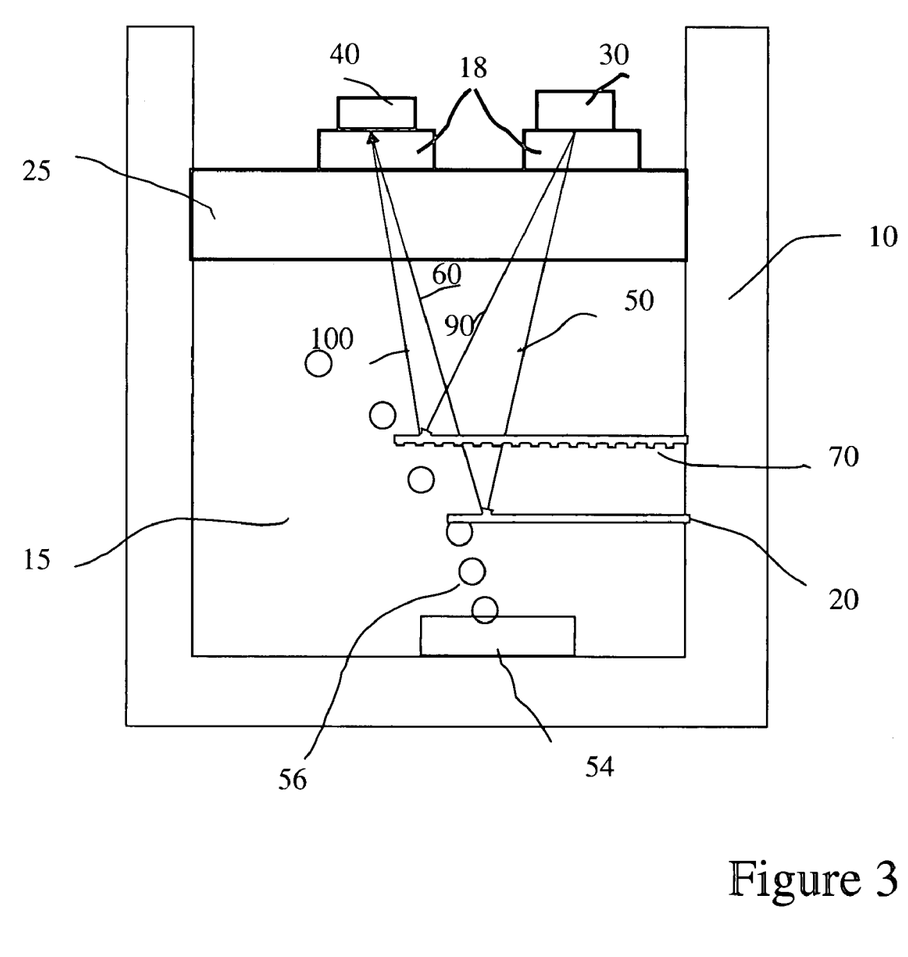
FIG. 3 is a schematic view of a nanomotion sensor having a pair of differentially operated cantilevers. One has a surface treatment layer prepared for interaction with the specimen and the other does not. The differential measurement of the combination allows for cancellation of environmental noise.

In an alternative embodiment, shown in FIG. 3, a differential measurement is described which is used to cancel environmental effects and noise. Here cantilever 20 having reflected beam 60 is mounted preferably side by side (schematically indicated in the figure) with treated cantilever 70 having second reflected beam 100, and the difference in photoresponse between reflected beam 60 and second reflected beam 100 is analyzed. This embodiment has the benefit in that it cancels and/or identifies the difference in the motion of the cantilever 20 and the treated cantilever 70 caused, for example, by the environment, such as liquid motion in the enclosure 10 or by cells 56 that collide with cantilever 20 but do not bind.

Other Embodiments of the NMS

In yet another embodiment, multiple cantilevers can used, with some cantilevers carrying specific probe molecules and the other cantilevers carrying a non-specific probe molecules or no probe molecules. Multiple cantilevers organized in such a fashion are known as an array of cantilevers. The cantilevers of the array may be grouped in pairs, each pair including one cantilever for sensing motion and binding or retention time and one neutral or reference cantilever. The difference between signals of each cantilever pair in the array as shown in FIG. 3 provides the net differential signal for that pair. Note: Retention time is defined as the length of time, relative to a standard or absolute, that the sample interacts with or binds to the NMS.

In addition, multiple NMS cantilevers can also be arranged in parallel or in series using a combination of numerous Integrated NMS Systems ganged together. Since the Integrated NMS System is small in size, multiple units of the Integrated NMS System, each containing one or more NMS cantilevers, a NMS measurement chamber and a complete optical lever-type detection system. Such a configuration, containing several, dozens or even hundreds of Integrated NMS Systems, supported by fluidics, could be enclosed in a single self-contained instrument.

An another embodiment of the invention allows for a convenient method of calibration of cantilever force constant, prior to performing measurements in the NMS. Here, a carrier fluid or gas, either passively or actively, allows a calibration standard (e.g., sulfate terminated latex spheres) to enter into the vicinity of the NMS cantilever, where the cantilever is of known resonance frequency, as measured by the NMS for example. The binding of the calibration standard to the cantilever causes a shift in the cantilever oscillation, whether actively or thermally driven, that allows calibration of the cantilever's force constant. The calibration standard could be facilitated by numerous materials and methods, for example by metal colloids or fluid or gas pressures acting on the cantilever, and so is not limited to the examples we provide. Calibrations could also be performed independently of the NMS using established methods such as the "added-mass" method.

With a cantilever or an Integrated NMS array, it is possible to introduce a complex sample mixture containing many types of specimens into the flowing liquid medium encompassing the array and to identify and characterize the complex mixture by monitoring the electrical output from the photodetector of the Integrated NMS array. The number of cantilevers or pairs of cantilevers forming the array is nearly unlimited. Such a cantilever or Integrated NMS array has practical utility in both biomedical and environmental applications. An example of an environmental application would be to use such a detector to identify an unknown contaminant in a sample of air or water.

In still yet another embodiment, specimen motion is generated via a carrier gas, colloidal suspension or liquid which is allowed to flow into the vicinity of the NMS. In a another embodiment, specimen motion is generated via an electric or magnetic field which then makes it possible for the specimen to move into the vicinity of said sensor. A sample is a collection of specimens in any material or liquid or suspension. Sample motion is generated either by self-propulsion or by a motion-facilitator. A motion facilitator is, for example a carrier fluid moving under conditions of continuous or discontinuous flow In another embodiment of the invention, the concentration of specimens within a sample is measured by determining the frequency at which individual specimens of the sample collide or interact with the NMS and generate a motion signal.

Another embodiment of the invention involves collection of a specimen of the sample that is retained at the cantilever due to its physisorption or chemisorption to the cantilever. In this embodiment, the specimen is collected by aspiration through an adjacent port-hole machined into the side of the NMS chamber, or by simply breaking the cantilever free of its substrate and collecting the specimen and the cantilever.

This completes the general discussion of the NMS. To make the NMS practical, it is necessary to integrate it in order to provide reliability, low cost and ease of operation. An Integrated NMS is described below.

Integrated Nanomotion Sensor

Figure 4:
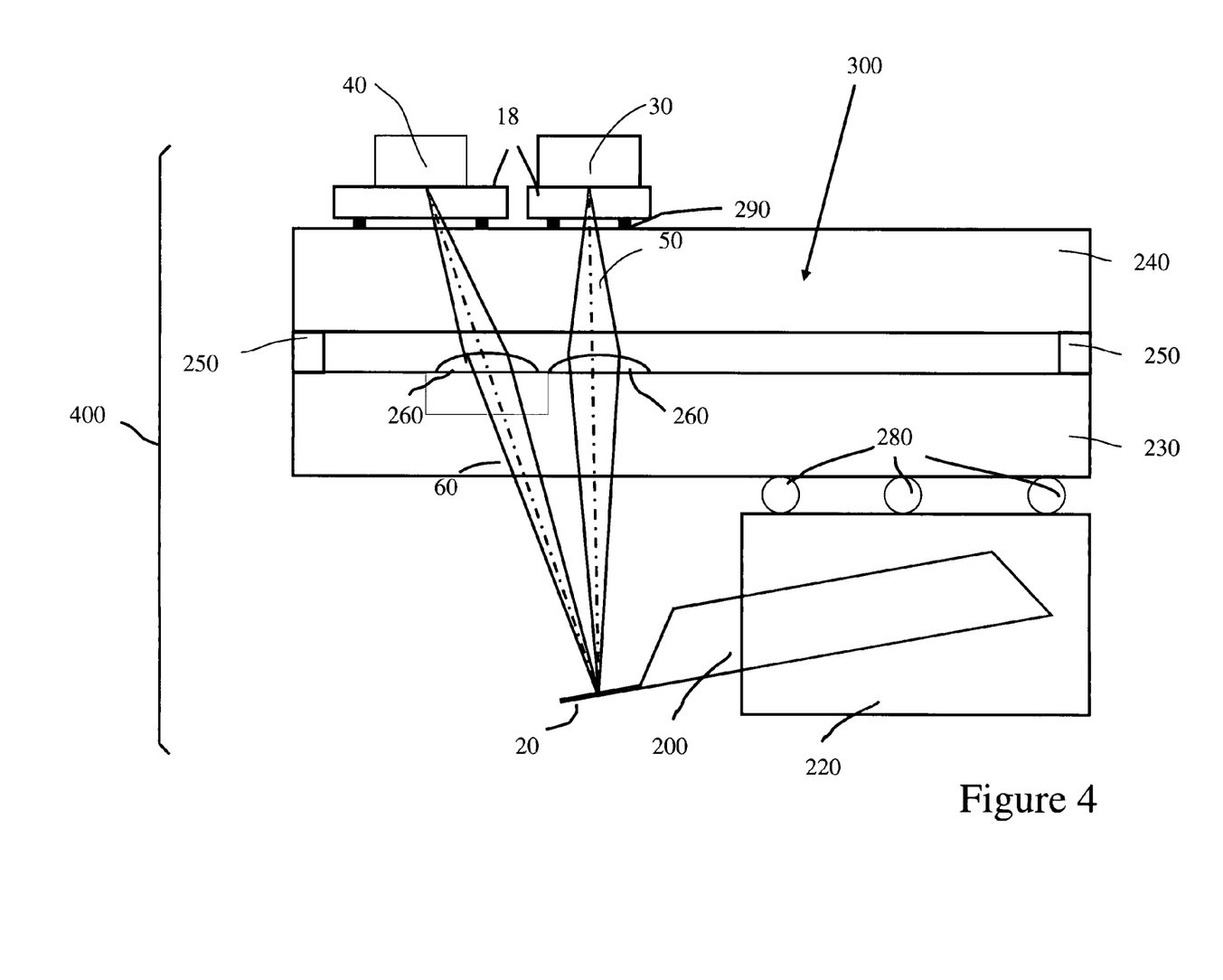
FIG. 4 is the preferred embodiment of an integrated nanomotion sensor.

FIG. 4 shows one embodiment of an Integrated NMS. Cantilever 20 is composed of a suitable material such as silicon or silicon nitride that is etched from a substantially more massive cantilever support 220 which is affixed at a predetermined angle to a cantilever support 220. Cantilever 20 is micromachined and has a length in the range between 10 um and 1000 um and preferably 400 um long, has a width in the range between 5 um and 100 nm and preferably 75 um wide and has a thickness which is in the range of xxx to xxx and preferably 1 um thick The length and width dimensions are dependent upon the material comprising the cantilever beam and are selected in order to achieve a soft lever configuration having a force constant in the range between 0.001 and 1000 Newton/meter and preferably having a force constant of 0.1 N/m. Use of a micromachined cantilever beam of nanometer dimensions enables the detection and characterization of forces in the range XX Newton to XX Newton. The response time of the Integrated NMS is determined by the resonance frequency of the beam of cantilever 20, ranging from 1 Hz to 100 MHz, and typically 100 kHz.

A laser 30 is affixed to an upper transparent substrate 240. Laser radiation is chosen to operate preferably in the visible part of the light spectrum, e.g. at 670 nm, for ease of alignment. However, an operating range in the infrared or ultraviolet range will perform equally as well.

A photodetector 40 is also affixed to upper transparent substrate 240 by means of metallized pads 290 using substrate fiducial marks, accurately aligned photolithographic masks and metal deposition steps as well known in the art of microelectronic circuit manufacture. Photodetector 40 can be any optical detector capable of tracking reflected laser light as known to one of ordinary skill in the art, for example, can be a split photodiode, linear array of photodetectors, piezo resistance elements or the like.

Upper transparent substrate 240 and lower transparent substrate 230 both have antireflection coatings. Lenses 260 can be formed integrally on the lower transparent substrate 230 using methods well known in the prior art, for example, by photoresist reflow or polymer molding. Refractive lenses 260 are shown in the figure but diffractive lenses such as Fresnel lenses are also possible. And can be formed integrally as well.

Assembly of a subassembly 300 is made as follows. Lower transparent substrate 230 and upper transparent substrate 240 have anti-reflection coatings of transparent substrates optimizes optical transmission of the incident and reflected laser beams through the transparent substrates and are fastened together with spacers 250. Proper alignment is obtained by having metallized pads, substrate fiducial marks, accurately aligned photolithographic masks and metal deposition steps as well known in the art of microelectronic circuit manufacture. Adhesion is achieved preferably by using ultraviolet-light-cured-adhesive that can be applied in liquid or thin film form and subsequently hardened when flooded with ultraviolet light to catalyze the adhesive. Materials comprising lower transparent substrate 230, upper transparent substrate 240 and spacers 250 are transparent to visible laser radiation and can include fused silica or other suitable materials. In this preferred embodiment, lower transparent substrate 230 and upper transparent substrate 240 are approximately 1 mm to 100 mm on a side and 0.1 to 10 mm thick.

In operation, laser 30 produces an incident beam 50 pointing downwards if a vertical cavity surface emitting laser is used. However, if an edge emitting laser is used, this would produce light horizontally and this would require a 45 degree reflecting mirror to produce the desired downwards direction of the incident beam 50. Incident beam 50 is then collimated through lens 260, affixed to lower transparent substrate 230, which focuses incident beam 50 directly onto cantilever 20 where it is reflected. Reflected beam 60 is then collimated by lens 260, affixed to a lower transparent substrate 230, which focuses reflected light directly on photodetector 40. This completes subassembly 300.

The primary design and manufacturing advantage of subassembly 300 the optical alignment portion of it is substantially coplanar and can therefore can be processed, aligned and bonded entirely in wafer form, prior to cutting into individual dies, where each die is a complete subassembly 300. This greatly increases the accuracy of assembly and greatly decreases the manufacturing cost of each die which is a main component of the NMS.

Finally, subassembly 300 in die form is affixed to cantilever support 220 in die form by solder ball contacts 280 using fabrication and alignment techniques known in the state of the art, in order to produce an Integrated NMS 400 as shown in its entirety in FIG. 4. The solder ball contacts 280 provide both alignment aid and adhesion. Instead of solder ball contacts 280, direct bonding of subassembly 300 to cantilever support 220 is possible, using fabrication and alignment techniques known in the state of the art.

It is seen that Integrated NMS 400 is actually partially integrated, with the most intricate and otherwise time-consuming optical alignment occurring on an integrated wafer level, while the affixing of components is accomplished by assembling on a die level. One of the benefits from the wafer level integration includes wafer scale fiduciary marks which are made using photolithography. Another advantage is that laser 20 need not be activated to achieve optical alignment.

Alternative Embodiment of Integrated NMS

Figure 5:
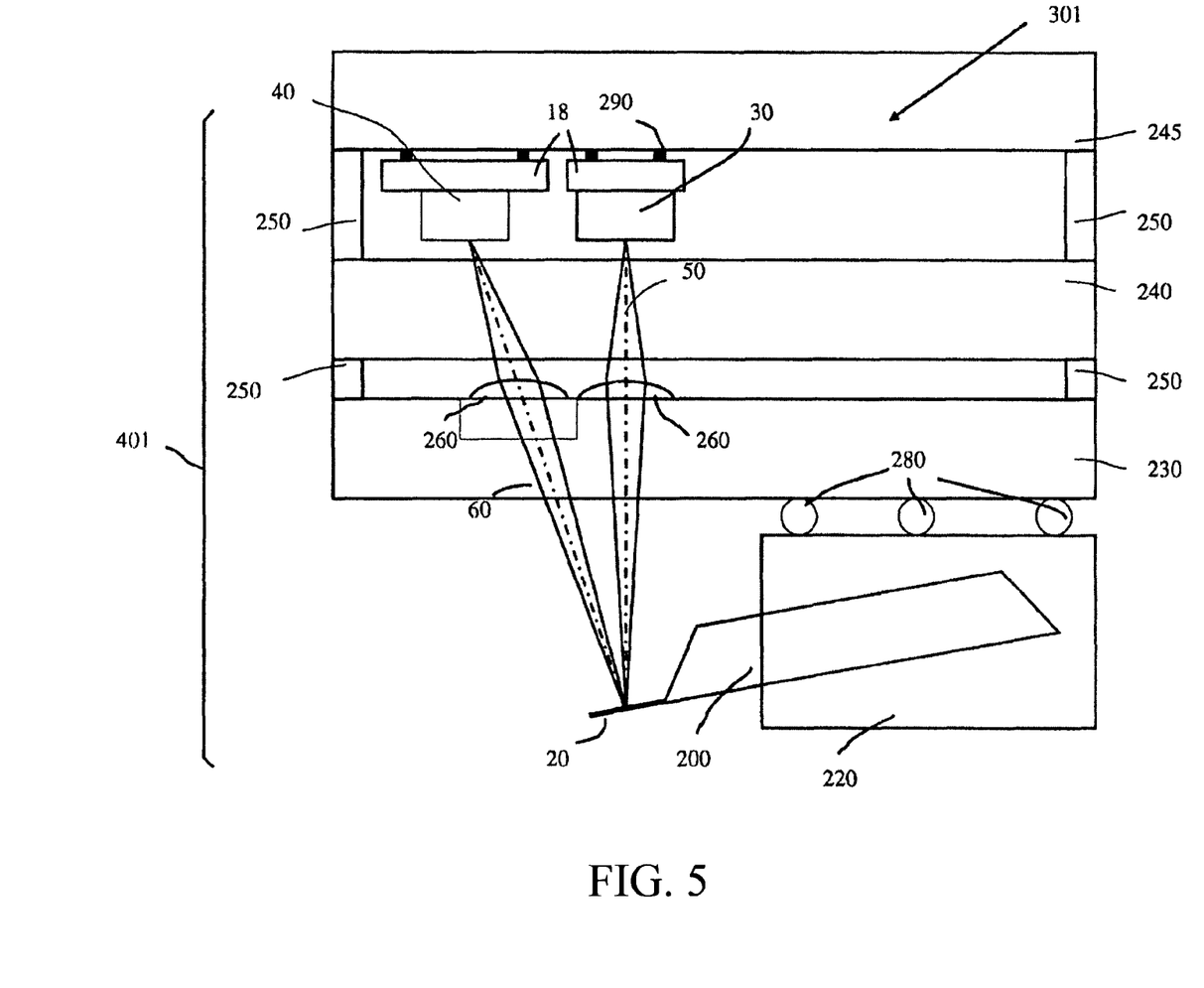
FIG. 5 is an alternate embodiment of an integrated nanomotion sensor.

FIG. 5 shows an alternative embodiment of involving three substrates instead of the two substrates shown in FIG. 4.

This alternative embodiment is identical to FIG. 4, except that laser 30 and photodetector 40 are affixed instead to a top substrate 245, which can be made of silicon, SiN fused quartz, etc, by means of metallized pads 290 using substrate fiducial marks, accurately aligned photolithographic masks and metal deposition steps as well known in the art of microelectronic circuit manufacture. The main benefit of selecting Si as a material for top substrate 245 is that metallization patterns can easily be generated in Si to provide power of operation for laser 30 and photodetector 40, and that output lines can be provided leading out from photodetector 40, all using standard Si processing techniques.

Assembly of a second subassembly 301 and second NMS 401 is made as follows. Top substrate 245 is fastened to upper transparent substrate 240 by means of spacers 150 and upper transparent substrate 240 is fastened to lower transparent substrate 230 by means of spacers 250. As in FIG. 4, proper alignment is obtained by having metallized pads, substrate fiducial marks, accurately aligned photolithographic masks and metal deposition steps as well known in the art of microelectronic circuit manufacture.

Alternative Designs

Figure 6:
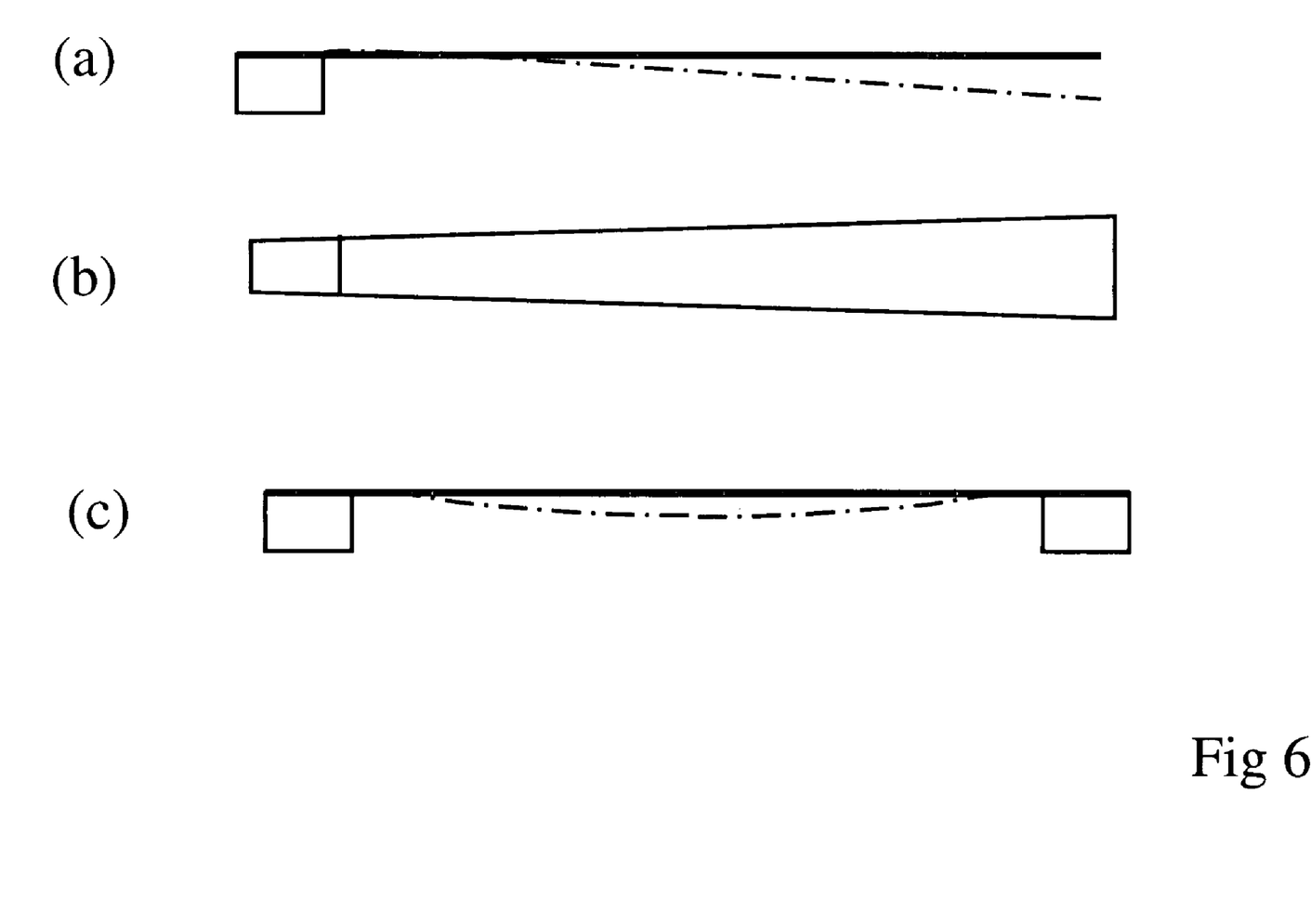
FIG. 6 shows the integrated nanomotion sensor positioned in a fluid having biological cells or other specimens.
Figure 7:
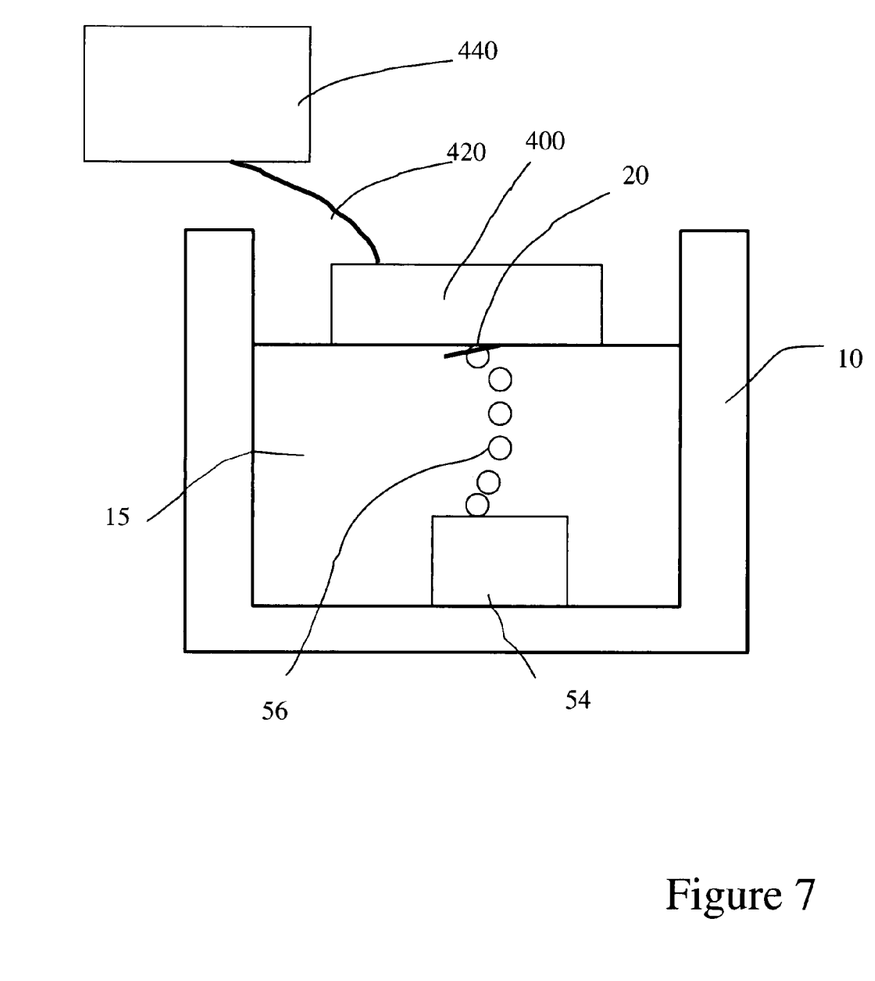
FIG. 7 shows various embodiments (a) cantilever as described above with uniform cross section, (b) cantilever with non-uniform cross section, and (c) ribbon supported at either end.

The cantilever described in the NMS as described above and shown schematically in FIG. 6(a) has an implied uniform width, but it can be generalized to a cantilever having a non-uniform width such as a trapezoidal cross section as shown in FIG. 6(b). Also the force transducing sensor aspect of the cantilever can also be accomplished by an alternative design shown in FIG. 6(c) which involves a doubly supported ribbon having supports on each end. The ribbon in FIG. 6(c) is shown with dimensions similar to the cantilever in FIG. 7(a) but the dimensions (length, width and thickness) as well as the materials selected can be quite different as needed for optimal response. The dashed line in FIG. 6(a) represents the deflection of the cantilever under applied force, and the dashed line in FIG. 6(c) represents the deflection of the doubly supported ribbon under applied force.

Operation

FIG. 7 shows the operation of Integrated NMS 400 which is very similar to the operation shown in FIG. 1 and has the same enclosure 10, fluid 15, cells 56, cell source 54, cantilever 20, and fluid surface 18. Integrated NMS 400, which is the preferred embodiment, is shown with cantilever 20 immersed in fluid 15, which may contain a specimen of some kind, for example, a colloidal suspension or biological cells or a solute. In general, fluid 15 can be any medium such as a gas, fluid, or in a vacuum or ultrahigh vacuum depending upon the application. Cell source 54 is immersed in fluid 15 which introduces cells 56 which can be a specimen of biological cells into fluid 15 by either of three main ways: (a) nonmotile cells immersed in continuously flowing fluid provided by a pump or gravity feed, (c) nonmotile cells immersed in a pulsed fluid like a P-shooter or (b) motile cells released in static fluid, or in combination thereof. The electrical output of the photodetector 40 is connected by a cable 420 to a computer 440 for appropriate analysis of the time-dependent data thereby obtained. By observing the dynamic response of computer 440 it is possible to infer the dynamic movements of cantilever 20, which can be related to the individual properties of cells 56 that impinge and accrue on it.

In actual experiments, sperm motility was measured at millisecond-to-microsecond temporal resolutions and the details are described below. Cantilever 20, of known force constant is used for sensing the sperm motion. Incident beam 50 is reflected off cantilever 20 creating reflected beam 60 that is detected by photodetector 40 which simultaneously records and displays at the computer screen the vertical and horizontal deflections and twists of cantilever 20 as motile sperm cells 56 swim into and interact with cantilever 20.

Tests are performed using live bovine sperm cells, live human sperms cells, and 45 µm diameter microspheres (moving in a flow of carrier fluid) as reference test specimens. Numerous motility characteristics are successfully recorded within several minutes using this NMS including, but not limited to, frequency, phase, amplitude, force, speed, energy, and work done. The vertical and horizontal deflections of the sensor (represented in volts, nanometers, nanoNewtons, nanometers per second, acceleration, Joules, # of ATP molecules, energy efficiency) show linear and non-linear swimming movements, individual cell and microsphere motions resulting in twist of the sensor, duration in microseconds-to-milliseconds of any of these characteristics, as well as the number of individual cells and microspheres hitting the sensor over time. The test results of the sensor demonstrate the wealth of information that can be obtained in a short period of time with practically no intervention required on the part of the user. The process is entirely automated following injection of the cell and/or microsphere suspensions into the nanomotion sensing chamber. Such a device requires very little training and minimal maintenance of parts.

In other tests, a coated cantilever is used that has an egg-like layer that is attractive for sperm. When the sperm arrives at the coated cantilever, it becomes selectively adsorbed on the coated cantilever, and its motility action is much more easily observed, than if the sperm would impact a similar but uncoated cantilever.

In still other tests, the impact or arrival and the residence time of certain cells can be observed on certain other substrates.

The nature of the interaction between cells and cantilever surface falls into three classes: (a) Impact, where the dynamic contact is made when a cell moving in a fluid contacts the cantilever and is detected as burst which is similar to a delta function, (b) Oscillation, where a motile cell, like a sperm cell, is adsorbed on the cantilever and causes the cantilever to oscillate, and (c) Accumulation, where cells continue to bind to a coated cantilever surface in such numbers that they can actually change the curvature and/or spring constant of the coated cantilever, which can be detected and can indicate the nature of binding kinetics to the coating. The latter case is important for rapid sampling of various biological materials and their binding behavior to a multiplicity of different coatings.

To increase the testing efficiency and to decrease the testing time, multiple cantilevers can be used in the form of an array. These can be manufactured by means known to the state of the art and can be grouped in pairs, each cantilever pair including one cantilever for physical and chemical sensing and one neutral or reference cantilever. The difference between signals of each cantilever pair in the array provides excellent and substantially noise-free information regarding binding between each combination of cell and coating on the cantilever.

Process

Figure 8:
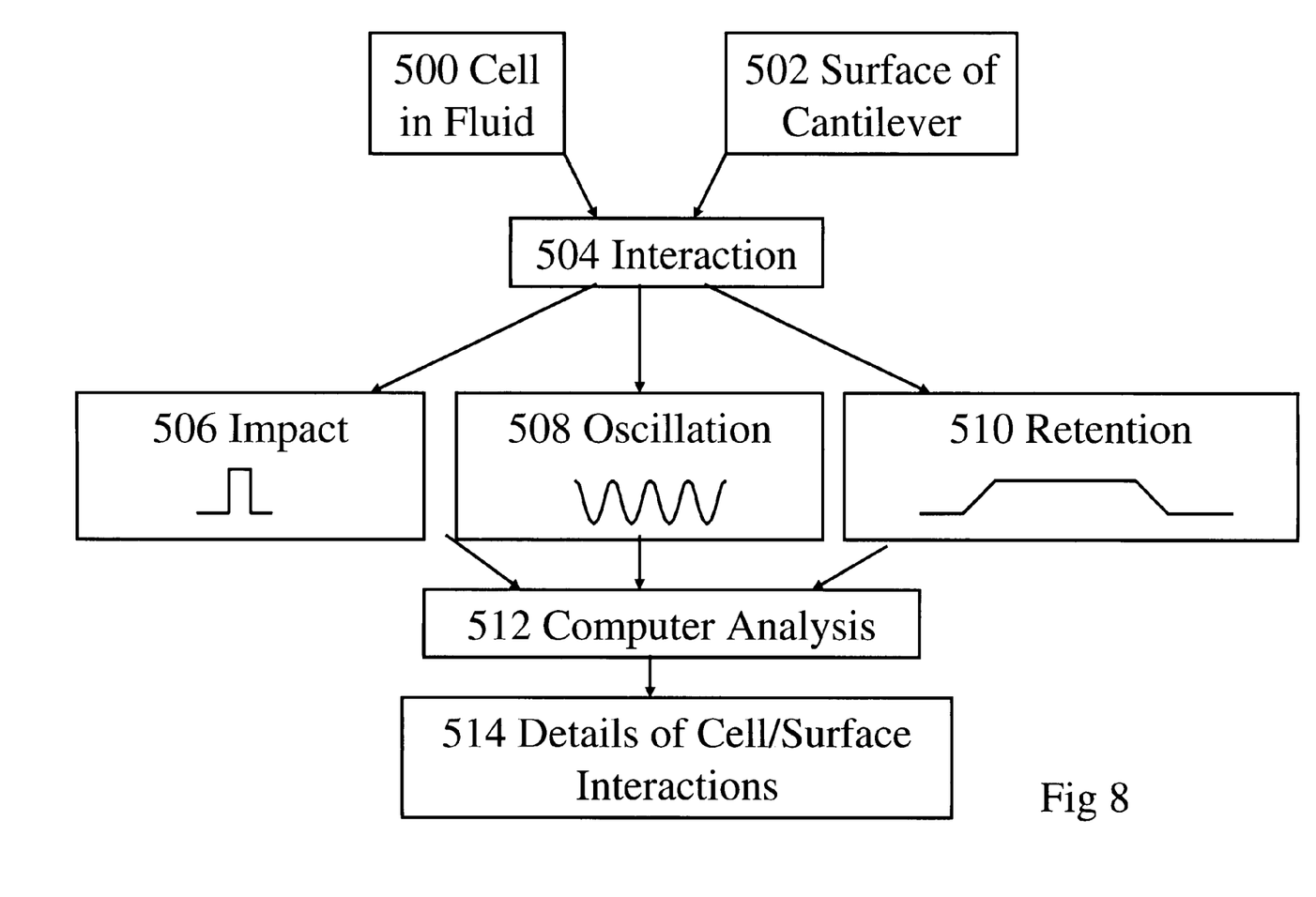
FIG. 8 shows the process flow.

The process used for operating and interpreting the results of the NMS or Integrated NMS is shown in FIG. 8. Reference is made to biological cells by example, but any other materials can be used as well.

Cells in a fluid 500 combine with the surface of a cantilever 502 to produce an interaction 504 with three effects: Interaction 504 can lead to an impact 506 where the dynamic contact is made when a cell moving in a fluid contacts the cantilever and is detected as burst which is similar to a delta function. Interaction 504 can lead to oscillation 508 a motile cell, like a sperm cell, is adsorbed on the cantilever and causes the cantilever to oscillate. Finally Interaction 504 can lead to retention 510 where cells continue to bind to a coated cantilever surface in such numbers that they can actually change the curvature and/or spring constant of the coated cantilever. The retention time can be detected and can indicate the nature of binding kinetics to the coating. The latter case is important for rapid sampling of various biological materials and their binding behavior to a multiplicity of different coatings. In the general case, two or more of these three interactions can be present at the same time. A Computer 512 is used to interpret the combined data flow from these effects and this leads to an understanding of the details of cell/surface interactions 514. This method can be employed to detect any physical or chemical interaction with high accuracy and at a low cost.

Although the description above contains many specificities, it should not be construed as limiting the scope of the invention but merely as providing illustrations of some of the presently preferred embodiments of the invention.

We claim:

1. A method for determining residence times of motile specimens on a force transducing sensor comprising the steps of:
   introducing a multiplicity of motile specimens in a medium into a motion sensor system comprising:
   an enclosed chamber adapted to receive a multiplicity of motile specimens;
   at least one force transducing sensor positioned within the chamber so as to be immersed in the medium during operation;
   force transducing sensor surface coatings having characteristics appropriate for the motile specimens; and
   a motion detector for detecting motion of the force transducing sensor caused by the motion of the motile specimens;
   measuring the motion of the force transducing sensor caused by the motion of the specimens, said measuring including the steps of:
   directing a sensing beam through a transparent substrate toward the force transducing sensor using a beam generator mounted on the transparent substrate; and
   receiving a reflected beam through the transparent substrate from the force transducing sensor using a beam detector mounted on the transparent substrate; and
   calculating the residence times of the motile specimens on the force transducing sensor surface coatings from the motion of the force transducing sensor, wherein an interaction of the motile specimens with the force transducing sensor as a result of the motion of the motile specimens is categorized as one of an impact, an oscillation, and a retention to facilitate identifying a binding behavior of the motile specimens.

2. The method of claim 1 wherein the motile specimens are part of a biological sample.

3. The method of claim 1 wherein the force transducing sensor surface coatings are biologically active surface coatings.

4. The method of claim 1 wherein the force transducing sensor is a MEMS device.

5. The method of claim 4 wherein the MEMS device is a cantilever.

6. The method of claim 5 wherein the MEMS device includes at least two cantilevers.

7. The method of claim 6 wherein one cantilever is a reference cantilever with a biologically inactive surface coating.

8. A method for detecting motion of motile specimens within a medium, said method comprising:
   introducing into an enclosed chamber a medium having therein a multiplicity of motile specimens moving within the medium with a motile frequency;
   disposing at least one force transducing sensor within the chamber so as to be immersed in the medium during analysis and to interact dynamically with the motile specimens;
   directing the motile specimens at the at least one force transducing sensor;
   sensing a dynamic interaction of the motile specimens with the at least one force transducing sensor by directing a beam through a transparent substrate toward the at least one force transducing sensor using a beam generator mounted on the transparent substrate and detecting a reflected beam through the transparent substrate from the at least one force transducing sensor using a detector mounted on the transparent substrate, the transparent substrate forming a wall of the chamber; and
   determining the characteristic motile frequency of the motile specimens by detecting the dynamic interaction of the motile specimens with the at least one force transducing sensor via changes in a signal detected by the detector to facilitate measuring a concentration of the motile specimens in the medium.

9. The method of claim 8 wherein the motile specimens are biologically motile.

10. The method of claim 9 wherein the motile specimens are sperm.

11. The method of claim 8 wherein the force transducing sensor is a MEMS device.

12. The method of claim 11 wherein the MEMS device is a cantilever.

13. A method for determining characteristics of a motile specimen under analysis comprising the steps of:
   positioning at least one force transducing sensor within a chamber adapted to receive the motile specimen under analysis;
   directing motile specimens in a fluid toward a surface of the at least one force transducing sensor at an angle substantially orthogonal to the surface;
   causing an interaction of the motile specimens with a coating on the surface capable of interacting with the motile specimens;
   allowing the motile specimens to interact with the force transducing sensor; and
   detecting a measureable characteristic of the motile specimens in accordance with the interaction with the force transducing sensor using a beam directed through a transparent substrate toward the at least one force transducing sensor and a beam reflected by the at least one force transducing sensor through the transparent substrate, the transparent substrate forming a wall of the chamber, wherein the interaction of the motile specimens with the force transducing sensor as a result of the motion of the motile specimens is categorized as one of an impact, an oscillation, and a retention to facilitate identifying a binding behavior of the motile specimens.

* * * * *